(12) United States Patent
Bowman et al.

(10) Patent No.: US 12,274,449 B2
(45) Date of Patent: *Apr. 15, 2025

(54) EMBOLIC DELIVERY

(71) Applicant: MicroVention, Inc., Aliso Viejo, CA (US)

(72) Inventors: Heath Bowman, Aliso Viejo, CA (US); Kaushik Joshi, Aliso Viejo, CA (US)

(73) Assignee: MicroVention, Inc., Aliso Viejo, CA (US)

( * ) Notice: Subject to any disclaimer, the term of this patent is extended or adjusted under 35 U.S.C. 154(b) by 783 days.

This patent is subject to a terminal disclaimer.

(21) Appl. No.: 17/337,302

(22) Filed: Jun. 2, 2021

(65) Prior Publication Data

US 2021/0282787 A1    Sep. 16, 2021

Related U.S. Application Data

(63) Continuation of application No. 16/146,538, filed on Sep. 28, 2018, now Pat. No. 11,051,824.

(Continued)

(51) Int. Cl.
*A61B 17/12* (2006.01)
*A61B 17/00* (2006.01)

(52) U.S. Cl.
CPC .. *A61B 17/12145* (2013.01); *A61B 17/12022* (2013.01); *A61B 17/12113* (2013.01); *A61B 17/12172* (2013.01); *A61B 2017/00309* (2013.01); *A61B 2017/00477* (2013.01); *A61B 2017/1205* (2013.01); *A61B 2017/12054* (2013.01); *A61B 2017/12063* (2013.01); *A61B 2017/12068* (2013.01)

(58) Field of Classification Search
CPC ........ A61B 17/12145; A61B 17/12022; A61B 17/12113; A61B 17/12172; A61B 2017/00309; A61B 2017/00477; A61B 2017/1205; A61B 2017/12054; A61B 2017/12063; A61B 2017/12068
See application file for complete search history.

(56) References Cited

U.S. PATENT DOCUMENTS 3,591,819 A * 7/1971 Laing ........................ H02K 1/16
310/264
5,123,642 A * 6/1992 Stokes ................. A63B 63/083
473/489

(Continued)

FOREIGN PATENT DOCUMENTS

CA    3012247 A1 *  4/2007  ....... A61B 17/12022
CA    2681663 A1 * 10/2008  ....... A61B 17/12022
(Continued)

*Primary Examiner* — Tan-Uyen T Ho
*Assistant Examiner* — Osama Nemer
(74) *Attorney, Agent, or Firm* — Inskeep IP Group, Inc.

(57) ABSTRACT

Concepts related to embolic delivery, including embolic detachment systems and an embolic pusher retention mechanisms are discussed herein. An occlusive delivery device for embolic delivery can include a delivery pusher, an occlusive device comprising one or more wires and having a collapsed configuration when within a delivery catheter and an expanded configuration when not within the delivery catheter, a connection interface, and a retention structure connected to the connection interface and the occlusive device.

20 Claims, 13 Drawing Sheets

Related U.S. Application Data

(60) Provisional application No. 62/564,952, filed on Sep. 28, 2017.

(56) References Cited

U.S. PATENT DOCUMENTS

| | | | | |
|---|---|---|---|---|
| 5,562,725 A * | 10/1996 | Schmitt | ................... | D04C 1/06 623/1.53 |
| 5,591,222 A * | 1/1997 | Susawa | ..................... | A61F 2/90 623/921 |
| 5,733,294 A * | 3/1998 | Forber | ............. | A61B 17/12022 606/151 |
| 5,741,429 A * | 4/1998 | Donadio, III | ..... | A61M 25/0043 216/48 |
| 5,925,060 A * | 7/1999 | Forber | ............. | A61B 17/12109 606/191 |
| 5,989,242 A * | 11/1999 | Saadat | ............. | A61B 17/12145 606/1 |
| 6,267,783 B1 | 7/2001 | Letendre et al. | | |
| 6,652,396 B2 * | 11/2003 | McBride | .............. | A63B 63/083 473/485 |
| 8,043,326 B2 * | 10/2011 | Hancock | .......... | A61B 17/12022 606/200 |
| 9,439,663 B2 * | 9/2016 | Johnson | ............... | A61B 17/221 |
| 9,895,519 B2 * | 2/2018 | Harari | ................... | A61M 29/00 |
| 10,328,322 B1 | 6/2019 | King | .................... | A63B 63/083 |
| 10,398,441 B2 * | 9/2019 | Warner | ................ | A61F 2/0105 |
| 10,828,037 B2 * | 11/2020 | Divino | ............. | A61B 17/12172 |
| 11,540,838 B2 * | 1/2023 | Groff | ............... | A61B 17/12122 |
| 12,082,819 B2 * | 9/2024 | Rangwala | ........ | A61B 17/12036 |
| 2001/0023369 A1 * | 9/2001 | Chobotov | ................ | A61F 2/07 623/1.11 |
| 2004/0117004 A1 * | 6/2004 | Osborne | ................. | C25F 3/24 623/1.36 |
| 2005/0043755 A1 * | 2/2005 | Wilson | ............... | A61B 17/1219 606/200 |
| 2006/0271097 A1 | 11/2006 | Ramzipoor et al. | | |
| 2006/0276823 A1 | 12/2006 | Mitelberg et al. | | |
| 2008/0119887 A1 * | 5/2008 | Que | ................. | A61B 17/12022 606/103 |
| 2010/0063572 A1 * | 3/2010 | Teoh | .................. | A61B 17/0057 606/191 |
| 2010/0234872 A1 * | 9/2010 | Guo | ................. | A61B 17/12022 606/191 |
| 2011/0022149 A1 | 1/2011 | Cox et al. | | |
| 2011/0106128 A1 * | 5/2011 | Chen | .................. | A61B 17/1215 606/191 |
| 2012/0239133 A1 * | 9/2012 | Cartledge | ............... | A61F 2/064 623/1.15 |
| 2013/0131711 A1 * | 5/2013 | Bowman | ............ | A61B 17/1215 156/70 |
| 2013/0261657 A1 * | 10/2013 | Lorenzo | ........... | A61B 17/12113 606/200 |
| 2014/0058434 A1 | 2/2014 | Jones et al. | | |
| 2014/0303745 A1 * | 10/2014 | Anderson | .......... | A61B 17/7098 87/8 |
| 2015/0272589 A1 | 10/2015 | Lorenzo | | |
| 2016/0249934 A1 | 9/2016 | Hewitt et al. | | |
| 2016/0331377 A1 * | 11/2016 | Divino | ............. | A61B 17/1214 |
| 2017/0189033 A1 * | 7/2017 | Sepetka | ........... | A61B 17/1215 |
| 2017/0224355 A1 * | 8/2017 | Bowman | ................ | B29C 71/02 |
| 2018/0104077 A1 * | 4/2018 | Cartledge | ................. | A61F 2/93 |
| 2019/0142617 A1 * | 5/2019 | Pung | ........................ | A61F 2/82 623/1.12 |
| 2023/0146949 A1 * | 5/2023 | Guidotti | ........... | A61B 17/12172 604/509 |

FOREIGN PATENT DOCUMENTS

| | | | | |
|---|---|---|---|---|
| CA | 2399386 C | * | 11/2008 | ....... A61B 17/22032 |
| CA | 2734553 A1 | * | 3/2010 | ......... A61B 17/0057 |
| WO | WO-2005035020 A2 | * | 4/2005 | ....... A61B 17/12022 |

* cited by examiner

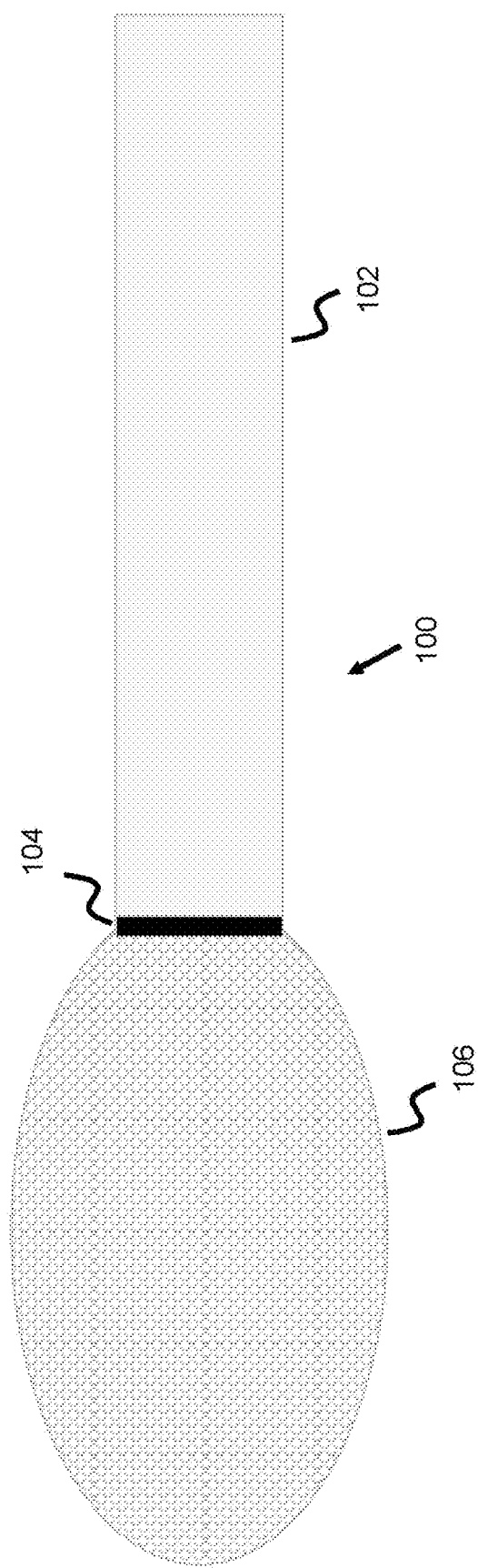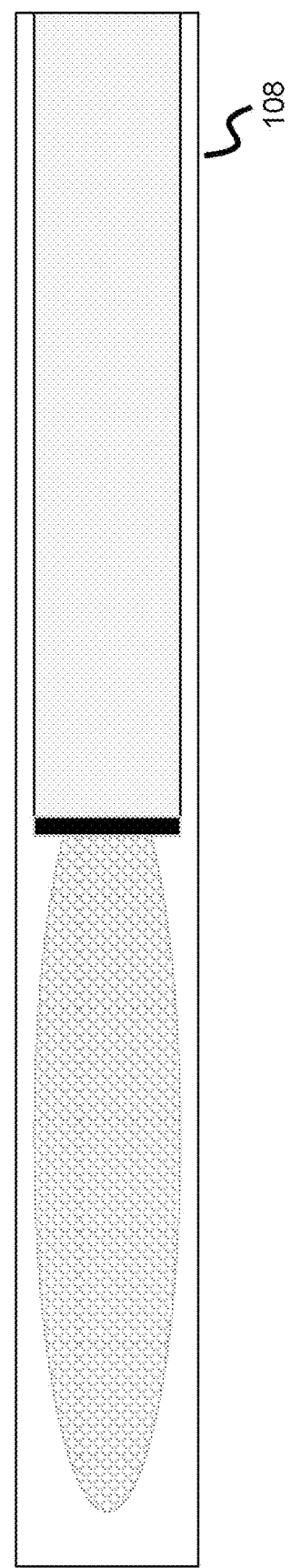
Figure 1a
Figure 1b

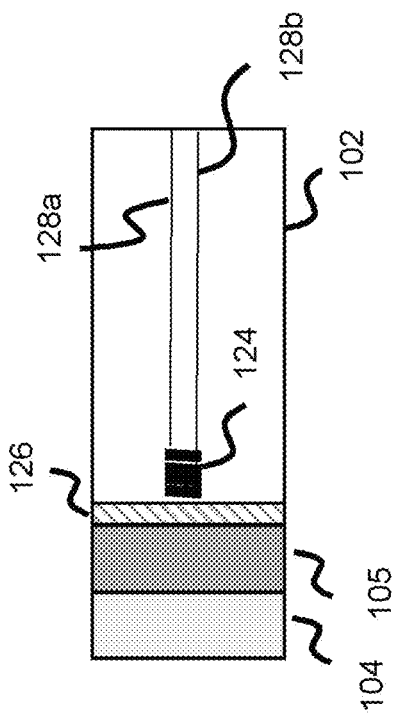
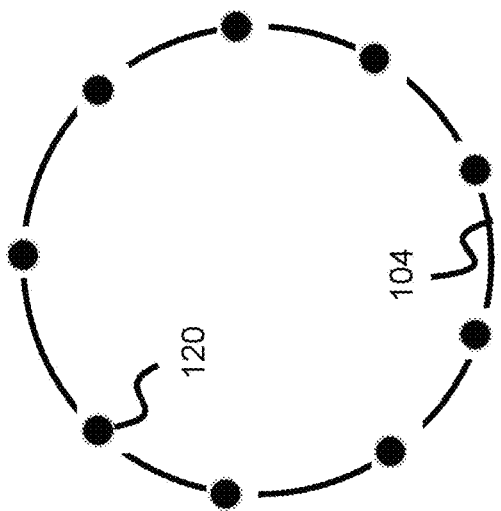
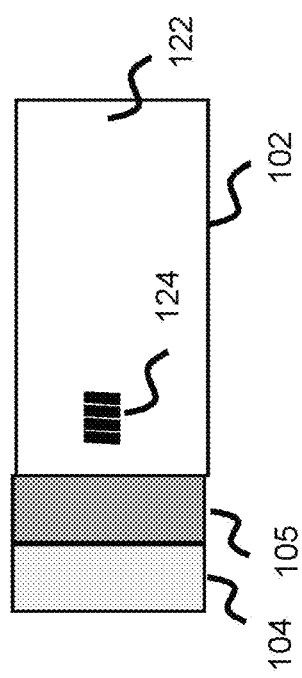
Figure 6a
Figure 6b
Figure 6c

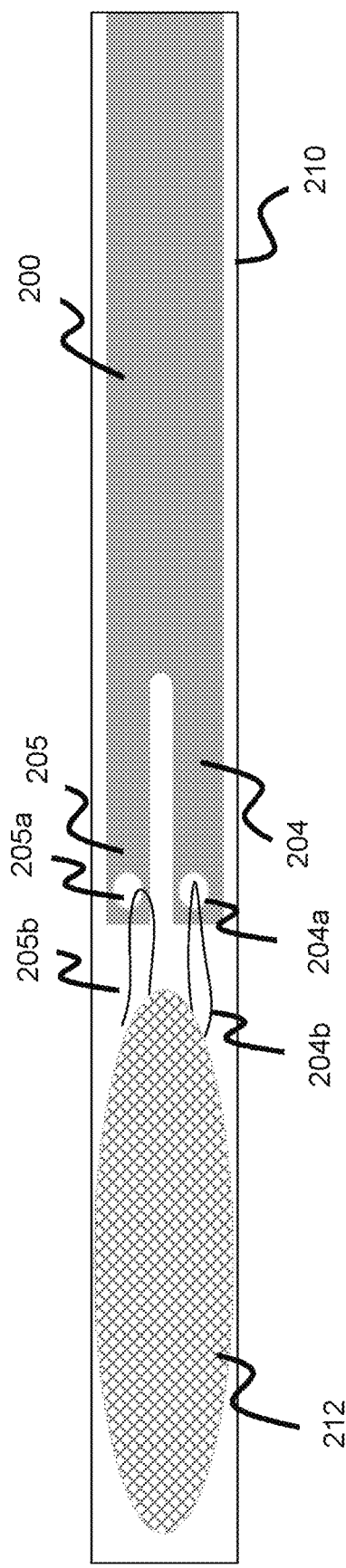
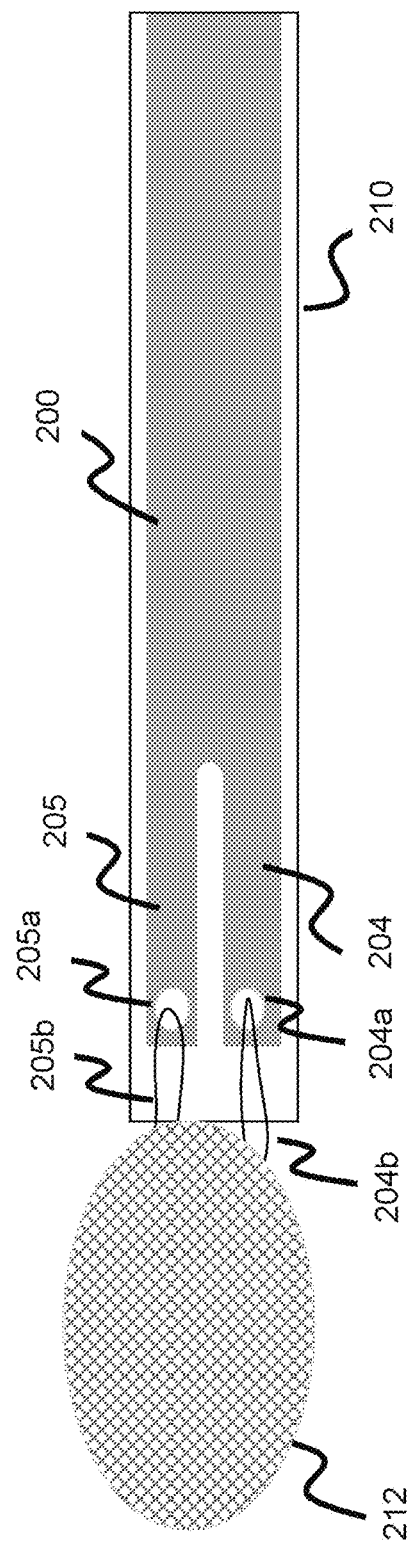
Figure 11
Figure 12

EMBOLIC DELIVERY

RELATED APPLICATIONS

This application is a continuation of U.S. patent application Ser. No. 16/146,538 filed Sep. 28, 2018 entitled Embolic Delivery, which claims benefit of and priority to U.S. Provisional Application Ser. No. 62/564,952 filed Sep. 28, 2017 entitled Embolic Delivery, both of which are hereby incorporated by reference in their entireties.

BACKGROUND OF THE INVENTION

Embolic material—including embolic coils and embolic meshes are used for a variety of occlusive therapeutic purposes in the vasculature, such as, but not limited to, occluding aneurysms, vessel shutdown, left atrial appendage occlusion, treating arteriovenous malformations and fistulas, and fallopian tube occlusion. These embolic materials can be particularly small especially when used in the neurovasculature—for instance, when used to treat neurovascular aneurysms. A relatively newer category of embolic material known as intrasaccular devices generally comprises meshes that conform to the shape of a portion of the treatment site to promote occlusion. These embolic devices are generally delivered via a pusher that the embolic material is connected to, where the pusher is pushed through a delivery catheter and a detachment system then detaches the embolic material from the pusher.

Detaching the embolic material from the pusher upon delivery can be complicated, especially as these embolic or occlusive devices are sized down to treat smaller target regions. Another problematic area involves the situation when the embolic material is pushed out from the delivery catheter and adopts its natural expansile shape, which can create delivery problems—including kickback and high delivery force—due to the sudden shape change which the implant adopts. The following embodiments deal with systems, devices, and methods that address these issues.

SUMMARY OF THE INVENTION

In one embodiment, an occlusive device and/or an occlusive system is described. The proximal end of the occlusive device is connected to a connection interface attached to a delivery pusher, and wires of the occlusive device are wound around the connection interface.

In one embodiment, an occlusive device and/or an occlusive system is described. The proximal end of the occlusive device is connected to a connection interface attached to a delivery pusher. The connection interface includes one or more bands and the occlusive device is connected to the bands of the connection interface.

In one embodiment, an occlusive device and/or an occlusive system is described. The proximal end of the occlusive device is connected to a connection interface attached to a delivery pusher. The connection interface includes one or more openings that accommodates the occlusive device. In one embodiment, the connection interface additionally includes various cut-out regions to augment the flexibility of the connection interface.

In one embodiment, an occlusive device and/or an occlusive system is described. The proximal end of the occlusive device is connected to a connection interface attached to a delivery pusher. The connection interface includes one or more coils spanning around the connection structure, and the occlusive device is connected to portions of the one or more coils.

The following embodiments deal with a delivery and detachment system that can be used with embolic occlusive material, including intrasaccular devices.

In one embodiment, an occlusive device and/or an occlusive system is described. The occlusive device is connected to a delivery pusher and the distal portion of the delivery pusher has a heat-set flowering expanded shape.

In one embodiment, an occlusive device and/or an occlusive system is described. The occlusive device is connected to a delivery pusher and a mechanical severing mechanism can be tracked through the delivery pusher to detach the occlusive device from the delivery pusher.

In one embodiment, an occlusive device and/or an occlusive system is described. The occlusive device is connected to a delivery pusher and a thermal severing mechanism can be tracked through the delivery pusher to detach the occlusive device from the delivery pusher.

BRIEF DESCRIPTION OF THE DRAWINGS

These and other aspects, features and advantages of which embodiments of the invention are capable of will be apparent and elucidated from the following description of embodiments of the present invention, in which:

FIG. 1a illustrates an embolic delivery device, according to one embodiment.

FIG. 1b illustrates an embolic delivery device within a delivery catheter, according to one embodiment.

FIG. 6a illustrates attachment locations between a connection interface and a delivery pusher, according to one embodiment.

FIG. 6b illustrates a connection interface, intermediate structure, and delivery pusher, according to one embodiment.

FIG. 6c illustrates a connection interface, intermediate structure, and delivery pusher, according to one embodiment.

FIG. 11 illustrates a delivery pusher in a collapsed state connected to an occlusive device in a collapsed state, according to one embodiment.

FIG. 12 illustrates a delivery pusher in a collapsed state connected to an occlusive device in a partially expanded state, according to one embodiment.

DESCRIPTION OF EMBODIMENTS

Figure 2A:
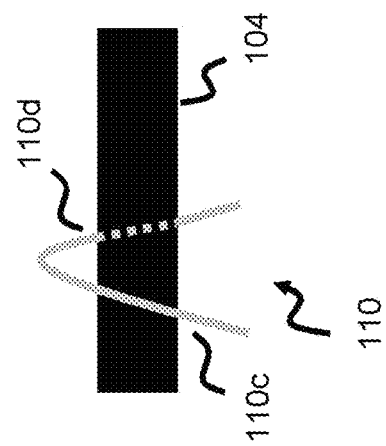
FIG. 2a illustrates a connection interface between a delivery pusher and an embolic device, according to one embodiment.

Specific embodiments of the invention will now be described with reference to the accompanying drawings. This invention may, however, be embodied in many different forms and should not be construed as limited to the embodiments set forth herein; rather, these embodiments are provided so that this disclosure will be thorough and complete, and will fully convey the scope of the invention to those skilled in the art. The terminology used in the detailed description of the embodiments illustrated in the accompanying drawings is not intended to be limiting of the invention. In the drawings, like numbers refer to like elements.

Embolic or occlusive devices are used for a variety of interventional purposes, for instance occluding or filling a target treatment space—such as an aneurysm, left atrial appendage, fistula, or vessel—in order to limit blood flow to the region. A certain class of embolic material called intrasaccular devices typically utilizes meshes to conform to the shape of the neck or ostium of the treatment site (e.g., aneurysm) to better occlude the treatment site to thereby limit blood flow to the region and better promote clotting over time.

For neurovascular procedures, such as occluding neurovascular aneurysms, unique complications are involved. The neurovascular blood vessels are small, and the embolic devices must also be small—first to fit within a catheter small enough to access the neurovascular vessels, and second to fit the relatively small target treatment sites. Creating usable embolic devices with this smaller environment in mind can be challenging for a variety of reasons. For instance, when the occlusive devices are delivered from a delivery catheter and adopt their heat set, expansile shape, significant force is generated which makes delivery difficult. Moreover, it can be difficult to design a detachment system to detach the occlusive device from the delivery pusher, especially as these occlusive devices are sized smaller to treat smaller vessels and smaller target areas. The following embodiments address these issues.

FIGS. 1a-1b illustrate an occlusion system 100 having an occlusive device 106 connected to a delivery pusher 102. The pusher 102 is used to deliver the occlusive device 106 through a catheter 108 and distally beyond the catheter to be delivered to a target treatment location. The distal end of the delivery pusher 102 is attached to a connection structure or connection interface 104 which connects to the occlusive device 106. In this way, the proximal end of the connection interface 104 is connected to the distal end of the delivery pusher 102, while the distal end of the connection interface 104 is connected to the proximal end of the occlusive device 106. The occlusive device 106 adopts a contracted, elongated configuration when housed in a delivery catheter (as shown in FIG. 1b) and its heat-set, expanded configuration when not within the delivery catheter (as shown in FIG. 1a). The delivery pusher 102 is typically quite long, at least as long as the delivery catheter 108 since the pusher is pushed through the entirety of the delivery catheter. For instance, for a neurovasculature procedure, the catheter must track a distance between the femoral artery (the typical entry point for such procedures) up into the neurovascular arteries, which can span several feet—so the pusher and catheter, for instance, can be 100-160 cm in length.

Occlusive device 106 can take on a variety of configurations, such as an occlusive intrasaccular mesh or an embolic coil. In one embodiment, the occlusive device is an intrasaccular device comprising a mesh of metallic wires—made of, for instance, nitinol, stainless steel, and/or radiopaque material such as tantalum, platinum, gold, or palladium. In another example, drawn-filled tubing, which comprises a radiopaque core material surrounded by a metallic (e.g., nitinol or stainless steel) jacket can be used as part of the metallic mesh to further aid in visualizing the occlusive device. Intrasaccular devices, including various intrasaccular embodiments, are described in US Publication Numbers 20141200607 and 20170224355, and U.S. Pat. Nos. 9,597,087, 9,918,720, 9,629,635, 9,955,976, 9,078,658, 9,198,670, 9,295,473, and 9,492,174—all of which are hereby incorporated by reference in their entirety, and all/any of which can be used as examples of occlusive devices delivered by the inventive devices/systems disclosed herein.

With typical intrasaccular devices, the proximal end of the device is welded directly to the pusher end, and some detachment means (e.g., thermolytic, electrolytic, or mechanical) are used to sever the occlusive device from the delivery pusher so that the occlusive device can be deployed. In practice, this would mean the wires comprising the proximal end of the occlusive device are welded directly to the interior or exterior of the pusher. Often, this involves a cylindrical radiopaque marker band attached at the distal end of the pusher, and the occlusive device proximal end wires being welded directly to the interior or exterior of this marker band. This marker band helps in visualizing the proximal part of the device and also provides an attachment point for the occlusive device. One problem with this welding approach is that the wires comprising the occlusive device have no freedom of movement when attached in this manner. The attachment junction between the proximal end wires of the occlusive device and the pusher are high stress areas and therefore as the wires adopt their naturally heat set, expanded shape upon being released from the delivery catheter, there is a lot of force being generated in a relatively small area. Therefore, as the occlusive device adopts its expanded shape, the delivery force is quite high. As a result, the user must push hard to get the occlusive device to exit the catheter, and there is often a lot of kickback as the device is being deployed. This kickback can be unpleasant for the operator/surgeon and can also result in the implant being improperly deployed. This fixed attachment structure also makes retraction back into the delivery catheter difficult, for instance, in circumstances where the implant needs to be repositioned.

FIGS. 2-5 show various connection interface embodiments between the proximal end of the occlusive device 106 and the pusher 102 which allow some "give" or movement of the proximal end of the occlusive device to distribute the delivery force and thereby minimize the associated delivery forces to avoid the complications discussed above. As mentioned above, the occlusive device 106 can be a metallic mesh comprising a plurality of wires—so the wires at the proximal end of the occlusive device 106 are connected to or linked to the connection interface.

Figure 2:
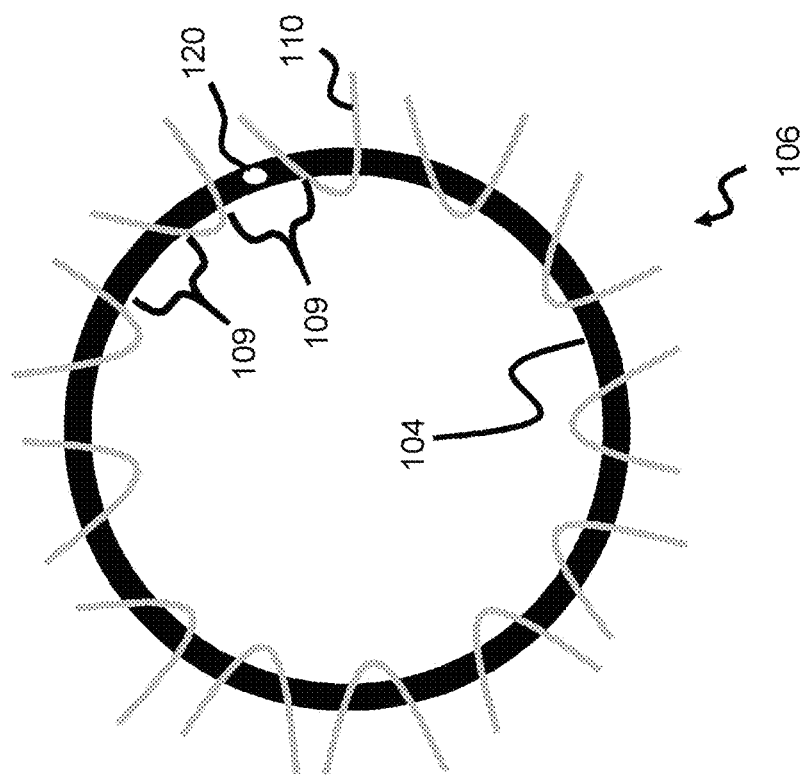
FIG. 2 illustrates a connection interface between a delivery pusher and an embolic device, according to one embodiment.

In one embodiment, shown in FIG. 2, the connection interface 104 is a thin ring and the wires 110 of the proximal or attached end of the occlusive device 106 are pulled around the ring such that the wires are looped or wrapped around the ring. This is done by pulling the wire behind the connection interface 104, then pulling the wire around the connection interface 104, and then pulling the wire in front of the connection interface 104—the end resulting being that a portion of the wire sits behind the connection interface. This is shown in FIG. 2a, where a portion 110c of wire 110 sits over a first side of the connection interface 104 (e.g., distal of the connection interface) and a portion 110d of the wire sits over a second side of the connection interface 104 (e.g., proximal of the connection interface). In this way, the wire of the occlusive device is secured to the connection interface 104, but in a way where the wire still has some degree of freedom of movement relative to the connection interface 104 since it is not attached to the connection interface.

Connection interface 104 is then attached to delivery pusher 102, however it is attached in such a way as to allow freedom of movement of the wires 110 of occlusive device 106. For instance, connection interface 104 is attached to the distal end of the pusher (e.g. through welding, adhesives, or other mechanical attachment means/structures) however these attachment points 120 are located in the spaces 109 between the wires 110 forming the proximal end of occlusive device 106. In this way, the wires 110 are not directly bonded to the pusher and thereby have some freedom of movement. FIG. 6a shows this configuration and can be thought of as the view directly behind the end of the connection interface 104 that is attached to delivery pusher 102—where the attachment points 120 are spread out in various locations along the connection interface. The attachment means can take on a variety of forms, including, for example, welding, adhesive, and/or other mechanical concepts. Due to this freedom of movement, as the occlusive device 106 is delivered from delivery catheter 108 and adopts its expanded shape, the occlusive device has some degree of give to reduce some of the delivery force, making deployment from the delivery catheter and retraction back into the delivery catheter (if needed) much easier.

Other attachment means between the delivery pusher 102 and connection interface 104 are also contemplated. For instance, both the delivery pusher 102 and connection interface 104 can include a plurality of holes around the periphery of each, where tethers are connected between these sets of holes so that the delivery pusher 102 and connection interface 104 are connected, but in a manner that still allows movement of wires 110. Alternatively, a plurality of small mechanical rods can be placed between the delivery pusher 102 and connection interface 104 and attached to each, these rods are circumferentially positioned around the proximal end of connection interface 104 and distal end of pusher 102, so as to mechanically bind the two structures, but again in a way that allows movement of wires 110.

Figure 2B:
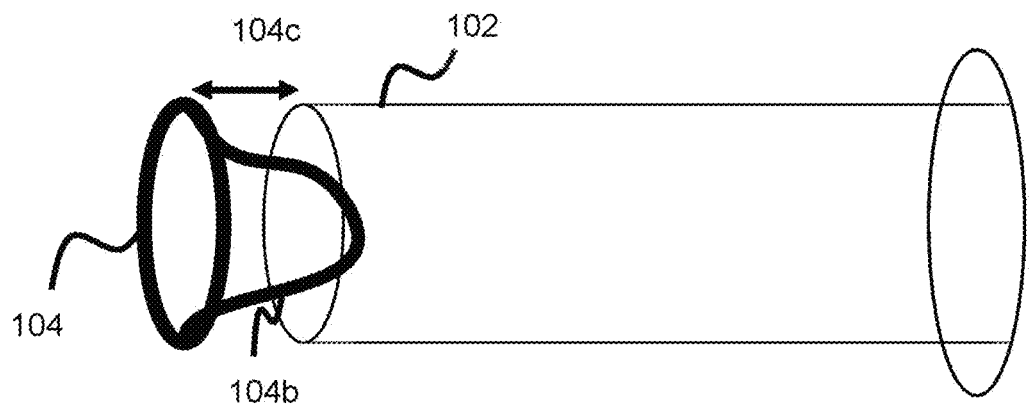
FIG. 2b illustrates a connection interface between a delivery pusher and an embolic device, according to one embodiment.

Different embodiments of the connection interface 104 can utilize various shape geometries to further enable enough space between the pusher and the connection interface to allow movement of the wires 110, given a segment of the wires 110 are in between the connection interface 104 and the pusher. In one embodiment, the proximal part of the connection interface 104 (the part of the connection interface 104 closest to pusher 102) has a number of inwardly curved or indented faces (e.g., forming a wavy shape) to allow more room for the wires 110. In one embodiment, the connection interface 104 takes the form shown in FIG. 2b where a portion of the connection interface projects inwardly into pusher 102. The connection interface 104 still comprises a ring shape, however a curved arc wire segment 104b proximally connects to the connection interface, projects inwardly into the pusher 102 and is attached to part of the pusher 102—in this way, the pusher 102 and connection interface 104 are connected through curved segment 104b. There is still a gap 104c between the connection interface 104 and delivery pusher 102, and the wires 110 of the occlusive device sit within this gap in the manner shown in FIGS. 2-2a. In this way, the wires have freedom of movement between the pusher 102 and connection interface 104. Different embodiments can utilize, for instance, a parabolic sheet having the topographical profile of the connection interface and curved segment 104b, where holes are cut into the sheet to accommodate wires 110. Other embodiments can utilize another similar attached, projecting structure 104b between the connection interface 104 and delivery pusher 102 which projects into the delivery pusher 102 and is attached to both the delivery pusher 102 and the connection interface 104. Again, the point here is to allow the wires to have some freedom of movement by providing space between the connection interface 104 and delivery pusher to accommodate a portion of wires 110. This freedom of movement will help minimize frictional and other forces during deployment of the implant, making implant delivery easier.

Figure 3:
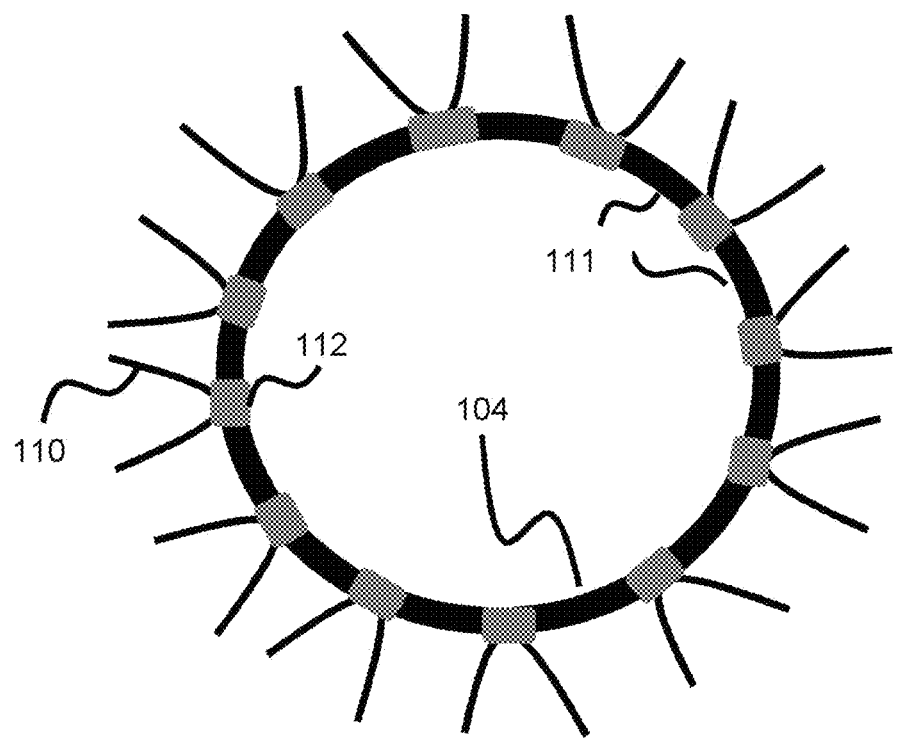
FIG. 3 illustrates a connection interface between a delivery pusher and an embolic device, according to one embodiment.

In another related embodiment shown in FIG. 3, the proximal end wires 110 of the occlusive device are connected directly onto rotatable bands 112. The bands have an inner diameter slightly larger than the outer diameter of the connection interface ring 104 and are not attached to the connection interface 104 and can therefore independently rotate over the connection interface 104. The wire ends 110 are directly connected (for instance, by welding or adhesive) to the rotatable bands 112. The connection interface 104 is attached to the distal end of the delivery pusher in such a way as to allow rotation of the bands, for instance by attaching the connection interface to the delivery pusher at locations 111 between the rotatable bands 112 (e.g., via welding, adhesive, mechanical rod structures, or other means) to enable free rotation of the bands. FIG. 6a, again, offers an example of how these attachment points can be spread around the connection interface 104. The embodiment of FIG. 2b can also be utilized as a way to connect the delivery pusher and the connection interface, where the bands would be mounted to the connection interface and the gap 104c would allow the bands to rotate freely; alternatively the connection interface 104 could be indented (e.g, forming a wavy shape), as discussed above, to allow room for the wires between the connection interface and delivery pusher. As the occlusive device 106 is freed from the delivery catheter, the proximal end of the occlusive device will be allowed to move since the proximal end wires 110 are connected to the rotating bands 112—thereby reducing some of the delivery force and ensuring an easier deployment and delivery. The rotating bands can be considered as a retention structure, retaining the wires while also allowing movement of the wires due to the ability of the bands to rotate over the connection interface 104.

Another related embodiment similar to the one shown in FIG. 3 would not have the proximal end of the wires connect to rotatable bands 112. Instead, the rotatable bands would contain a plurality of holes, and the wires would enter one hole, exit another hole and then continue to be wound back into the occlusive device—in this way, a portion of the wire is retained within the rotatable band.

Figure 4:
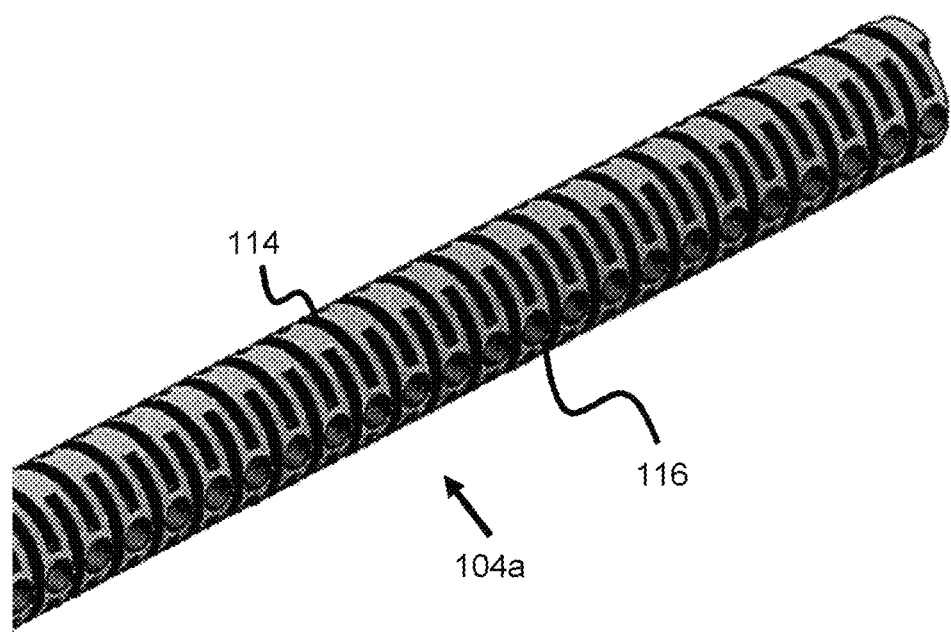
FIG. 4 illustrates a connection interface between a delivery pusher and an embolic device, according to one embodiment.
Figure 4B:
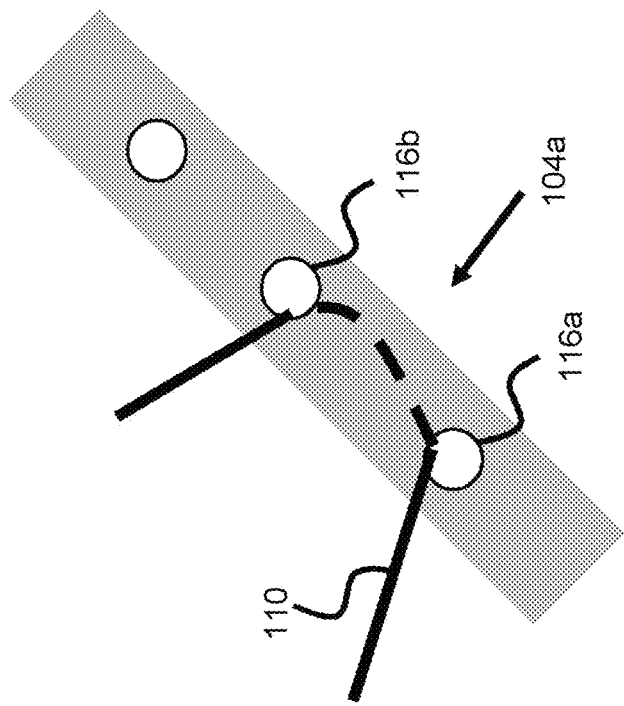
FIG. 4b illustrates a connection interface between a delivery pusher and an embolic device, according to one embodiment.
Figure 4A:
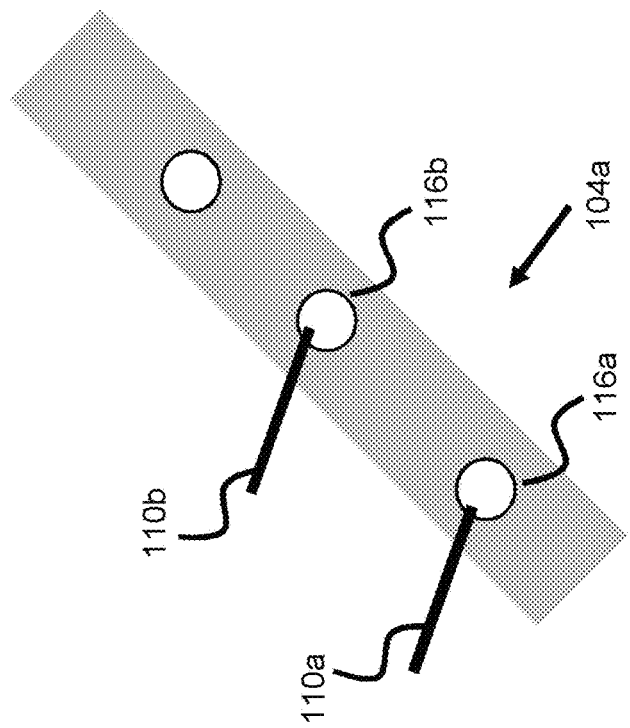
FIG. 4a illustrates a connection interface between a delivery pusher and an embolic device, according to one embodiment.

Another related embodiment is shown in FIG. 4, where the connection interface 104a is a flexible wire or tube with several cuts 114 bored into the surface (e.g., by laser, etching, mechanical cuts, or other means), where these cuts offer a flexible surface so the interface 104a can bend or make slight movements in response to force. The interface 104a also includes several holes 116, these holes accommodate the proximal end wires of the occlusive device, where the wires are bonded to the holes (for instance, by welding). These holes 116 can be considered as a retention structure used to retain the wires. In one example, each wire is positioned within a hole such that the proximal end of each wire terminates within its own, separate hole. Each wire can have an enlarged end which is contained within the hole, or each wire end can be mechanically affixed (e.g. through adhesive) within the hole. Another wire would then terminate in another hole. This configuration is shown in FIG. 4a where a first occlusive device proximal end wire 110a terminates in hole 116a of connection interface 104a, while another occlusive device proximal end wire 110b terminates in hole 116b. The holes that the wires terminate in can either be adjacent or non-adjacent, depending on factors including the size of the occlusive device, the number of wires used to wind the occlusive device, and the size of the connection interface. In another example, the wire is positioned through two holes such that the wire end is first placed in a first hole and then pulled out from a second hole. In this example a portion of the wire would physically sit underneath element 104a before tracking back out through another hole and then being wound back into the occlusive device. The wire could be pulled back out through either an adjacent hole, or a non-adjacent hole. This configuration is shown in FIG. 4b where a wire forming the proximal end of the occlusive device is pulled through hole 116a and out another hole 116b—in this manner, the wire is secured to the connection interface 104a by nature of being wound within and through a portion said connection interface. Various hole configurations are possible, for instance the holes can sit along a plurality of rows (or alternately, sit along various haphazard portions of the connection interface) and the wire can enter a hole of a first row, track through a portion of the connection interface, and exit a hole of another row—in this manner, a portion of the wire would be retained within part of the connection interface. In another example, the wire is tracked through the hole at the front end of the connection interface, through another hole behind the connection interface, and then back through another set of holes through the connection interface such that the wire ends up in front of the connection interface—in this manner, a portion of the wire would be retained behind the connection interface and another portion of the wire would be retained within the connection interface. The connection interface 104a is pulled into a circular ring shape where the two ends are welded together to produce a circular or ring-like connection interface shape like the ones shown in FIGS. 2-3. The interface 104a is then attached to the distal end of the delivery pusher. One advantage of this configuration is that connection interface 104a would not have to be connected at selected locations to the delivery pusher since the cut-out sections 114 allow some slight movement of the connection interface 104a and associated wires connected to the interface—however, the connection interface 104a could also be connected at selected intervals along the peripheral surface to the delivery pusher to further augment the amount of flexibility as the occlusive device is delivered—similar to the configuration shown in FIG. 6a and discussed earlier.

Figure 5:
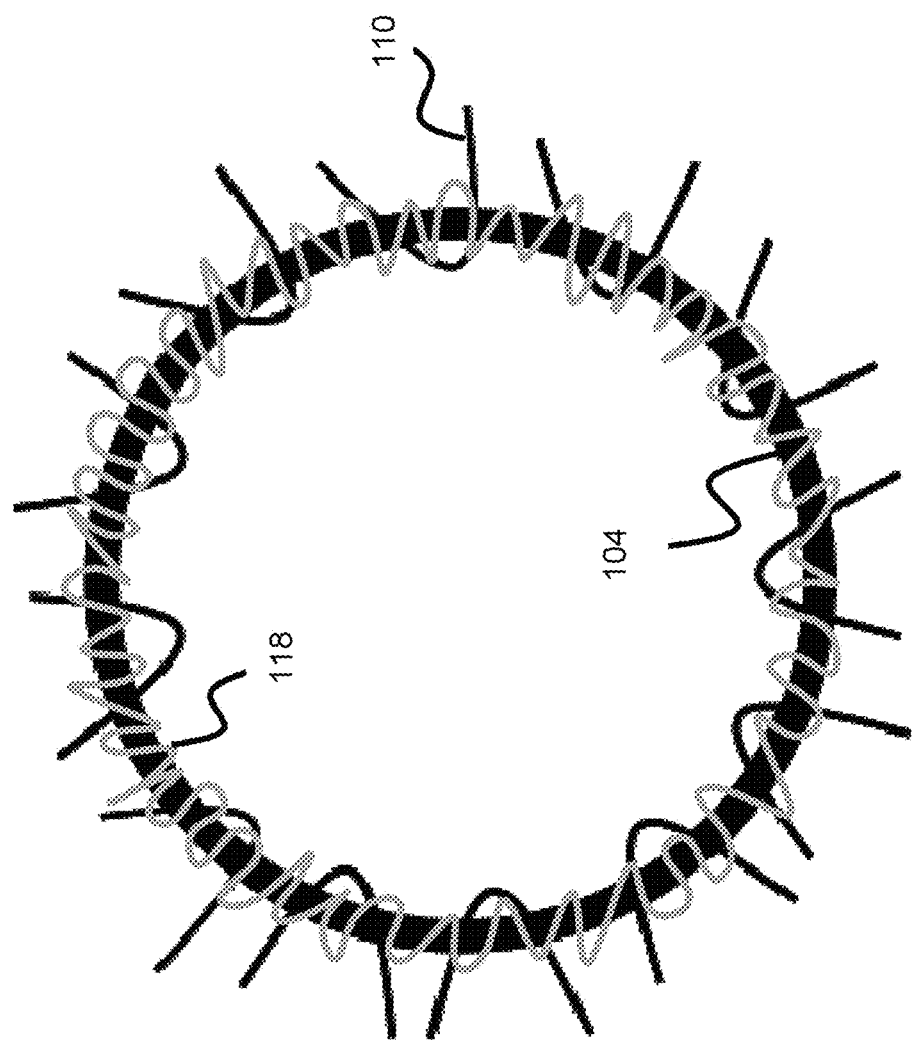
FIG. 5 illustrates a connection interface between a delivery pusher and an embolic device, according to one embodiment.

FIG. 5 offers another related embodiment where a connection interface 104 similar to that of FIGS. 2-3 is used. A coil 118 is wound around the connection interface 104 and the proximal occlusive mesh wire ends 110 are connected to the coil. The coil has some freedom of movement due to its coiled shape and can therefore distribute some of the delivery force as the associated occlusive device is delivered from the catheter. The wire ends 110 are affixed to the coil, through various mechanical means (e.g., welding, mechanical ties, adhesive, bands, or clamps). Though the figure shows the wire end as going past the coil, other embodiments can have the wire end 110 affixed directly to the coil such that the wire end 110 is flush with said coil. Alternative embodiments can utilize the segmented approach shown in FIG. 3 where various coils are placed around the connection interface 104 (where the various coils would replace the various rotating bands 112 of FIG. 3). The one or more coils can be considered as a retention structure, connected to and retaining the wires of the occlusive device while also allowing the wires to move in some capacity during delivery from the overlying delivery catheter. The connection interface 104 is preferably connected to the distal end of the delivery pusher in a segmented circumferential manner as shown in FIG. 6a (e.g., via periodic spot welds, adhesive bonds, and/or mechanical rod structures spaced around the periphery of connection interface 104) so that the coil is not stuck against the delivery pusher and retains some independent movement. Alternative embodiments can utilize the wires 110 being connected to both the connection interface 104 and the coil 118, or the wires 110 being connected directly to the connection interface 104. In these alternative embodiments, the coil will still have the ability to change shape (e.g., compress or elongate, both longitudinally and radially) to allow the wires to move a bit as the occlusive device is delivered from the delivery catheter. The connection interface can utilize an indented or wavy profile, as discussed earlier, or utilize the configuration shown in FIG. 2b to provide space between the connection interface and the delivery pusher—in these embodiments, the spaced attachment points of FIG. 6b would not need to be utilized since there naturally is space between the connection interface and the delivery pusher, and the wires of the occlusive device can fill all or part of this space.

Detachment means are also included in order to detach the occlusive device 106 from the delivery pusher 102. In one example, this detachment system is placed between the connection interface 104 and the delivery pusher 102, so that the connection interface 104 and connected occlusive device 106 detach from the delivery pusher 102. Such detachment means are well known in the art and can include mechanical, thermolytic, and/or electrolytic means. Thermolytic detachment systems are disclosed in U.S. Pat. Nos. 8,182,506, 9,414,819, 9,717,500, 8,932,317, 9,561,125, 9,867,622—all of which are hereby incorporated by reference in their entirety. These thermolytic systems typically utilize either a tether and a heater to heat and sever the tether, or an adhesive and a heater to melt the adhesive, and can be used to detach the connection interface from the pusher. For example, the severable tether or meltable adhesive can be placed between the connection interface 104 and the delivery pusher 102. Note, these concepts would typically utilize a tubular delivery pusher with a lumen therein since a heater (such as a heater coil) would sit within a distal section of the pusher lumen to melt or sever the attachment means (e.g., tether or adhesive) which are located in close proximity to the heater (e.g., abutting or next to the heater, or a tether which passes through the heater/heater coil).

In one example, one or more adhesive attachment points (like that shown in FIG. 6a) are located between connection interface 104 and pusher 102, the distal section of the pusher 102 lumen includes a heater element (e.g. heater coil) placed in close proximity to the adhesive(s) and the heat generated from the heater coil melts the adhesive attachment points to separate the connection interface 104 from the pusher 102. In another example, a sacrificial intermediate structure sits between connection interface 104 and pusher 102. The connection interface is welded or otherwise attached to the intermediate structure. A degradable or severable medium (e.g. a tether or adhesive) is between the delivery pusher and the intermediate structure, so that when the severable medium severs or melts, the intermediate structure, connection interface 104, and occlusive device 106 all detach together from the delivery pusher 102. With this concept, the connection interface 104 would then be attached to the intermediate structure instead of the pusher, and the intermediate structure contains the severable medium which enables the occlusive device 106 to detach from the delivery pusher 102. FIGS. 6b-6c show these embodiments. In FIG. 6b, connection interface 104 is proximally connected to intermediate structure 105 (for example, via the spread connection points of FIG. 6a), with intermediate structure 105 proximally connected to the delivery pusher 102. A tether 122 spans a portion of the pusher and distally terminates within intermediate structure 105, where the tether connects the intermediate structure to the delivery pusher. Delivery pusher 102 includes a heater (here, heater coil 124) which heats the tether to sever it to detach intermediate structure 105 and connection interface 104 from the delivery pusher 102. In FIG. 6c, a similar setup is used, except a meltable adhesive 126 connects the delivery pusher 102 to the intermediate structure 105. The heater 124 functions to melt the adhesive 126, thereby detaching pusher 102 from intermediate structure 105 and connection interface 104. Though not shown in FIG. 6b (but shown in FIG. 6c), a pair of wires 128a, 128b span the pusher and distally connect to the heater 124 to power the heater (these wires are proximally connected to a voltage source, such as a battery). The occlusive device is connected or otherwise linked to the connection interface 104, as described earlier, so that the occlusive device, connection interface 104, and intermediate structure 105 are all deployed within the vasculature.

Note, the embodiments described above and shown in FIGS. 1-6c generally utilize a connection interface linked to the proximal part of an occlusive device in such a manner as to allow the proximal portion of the occlusive device—which interfaces with the connection interface—to have some freedom of movement to make delivery of the occlusive device easier as the occlusive device is delivered from the delivery catheter. In some embodiments, the connection interface can be considered as separate from the delivery pusher where the connection interface and delivery pusher are connected—in this manner, the delivery pusher and occlusive device are operatively (but not directly) connected such that the delivery pusher still pushes or pulls the occlusive device. In some embodiments, the connection interface can be considered as part of the delivery pusher. For instance, where it is built directly onto the distal portion of the delivery pusher, or where the distal portion of the delivery pusher is configured in such a manner to act as a connection interface—an example of which would be creating a series of segmented channels around the pusher to leave room for the occlusive device wires as shown in FIG. 2, or than adding the rotating bands and/or coils of FIGS. 3 and 5, respectively). In some embodiments, the connection interface can be attached to the delivery pusher in alternate configurations—for instance, the connection interface can be placed radially over or radially within a distal portion of the delivery pusher rather than being attached to the distal end of the pusher.

Furthermore, in some embodiments (e.g., that of FIG. 2), the occlusive device and connection interface are connected or linked directly. In other embodiments, the occlusive device and connection interface are not connected directly, but rather linked indirectly through a retention structure (e.g. in FIG. 3 where wires 110 are connected to bands 112 which are placed over connection interface 104). In these other embodiments, though the connection interface and wires are not directly connected, they are operatively connected and linked through the retention structure.

Embolic delivery systems typically utilizing a mechanical delivery pusher connected to the embolic material, where some detachment means is used to detach the embolic or occlusive material from the delivery pusher. As the occlusive or embolic devices are sized down to treat smaller vessels and smaller target areas (e.g., neurovascular aneurysms), creating a detachment system poses additional challenges since there is less room to work with. The following embodiments deal with occlusive delivery concepts that address these issues.

Figure 7:
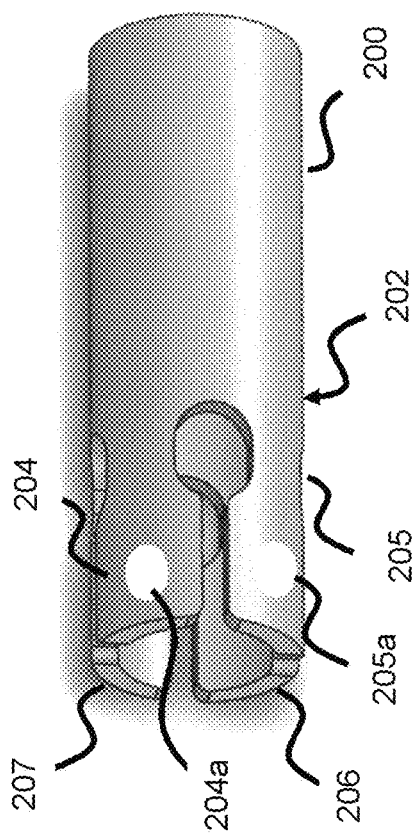
FIG. 7 illustrates a delivery pusher in a collapsed state, according to one embodiment.
Figure 8:
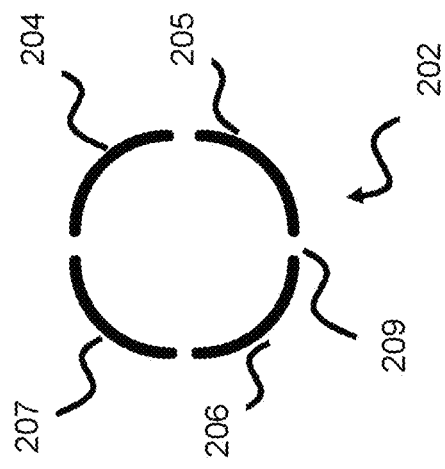
FIG. 8 illustrates a cross-sectional view of a delivery pusher, according to one embodiment.

FIG. 7 shows a delivery pusher 200 which connects to occlusive or embolic material (not shown here, though shown in later figures). Rather than showing the entire delivery pusher which can be long, the Figure simply shows the distal part of the delivery pusher. The occlusive or embolic material can be a variety of devices—such as, but not limited to, embolic coils and/or intrasaccular devices. FIG. 7 can be thought of as the angled side view of a delivery pusher 200. A distal portion 202 of the delivery pusher contains a plurality of arms 204, 205, 206, 207 which are separated by a small cut-out region or channel 209 between each arm. FIG. 8 offers a cross-sectional view from the front of the distal portion 202 of pusher 200, where each arm 204-207 is visible along with a gap between each arm representing the cut-out region or channel 209 between the various arms.

Figure 9:
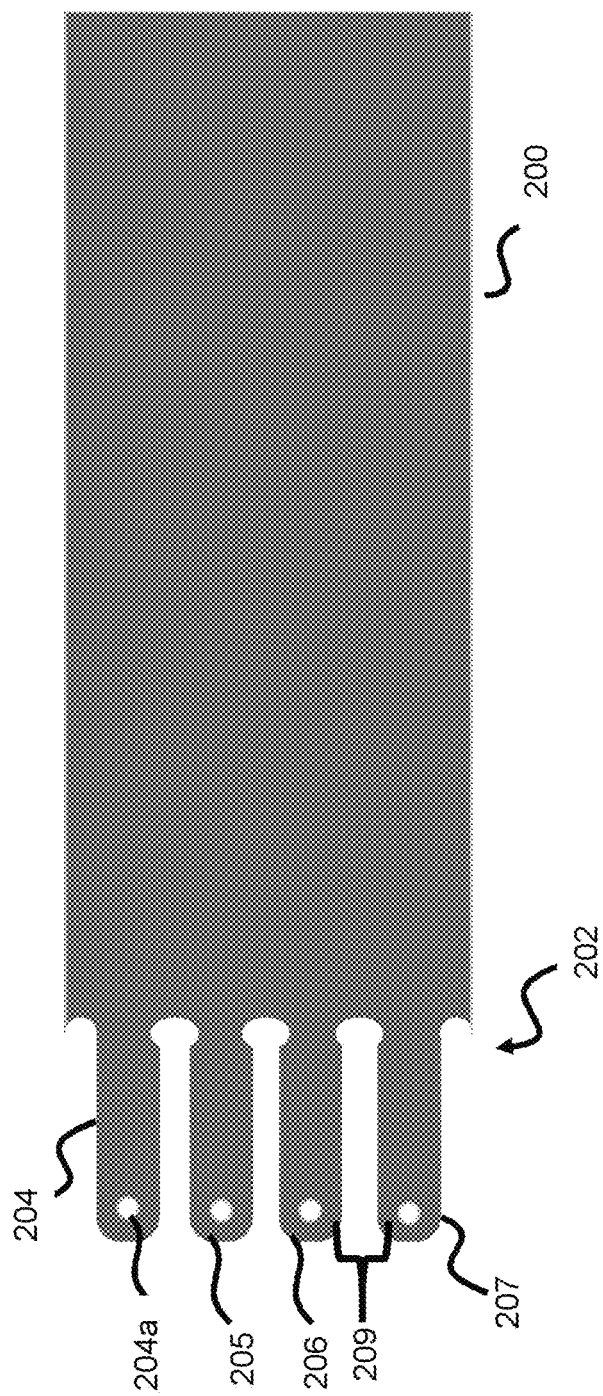
FIG. 9 illustrates a flattened view of a delivery pusher, according to one embodiment.

FIG. 9 shows the "rolled-out" view of FIG. 7; FIG. 9 can be thought of as a flat plate with distal protruding arms 204-207, where the flat plate is later rolled into a cylindrical configuration to provide the shape shown in FIG. 7. Arms 204-207 are separated by channels 209, as discussed above.

Figure 10:
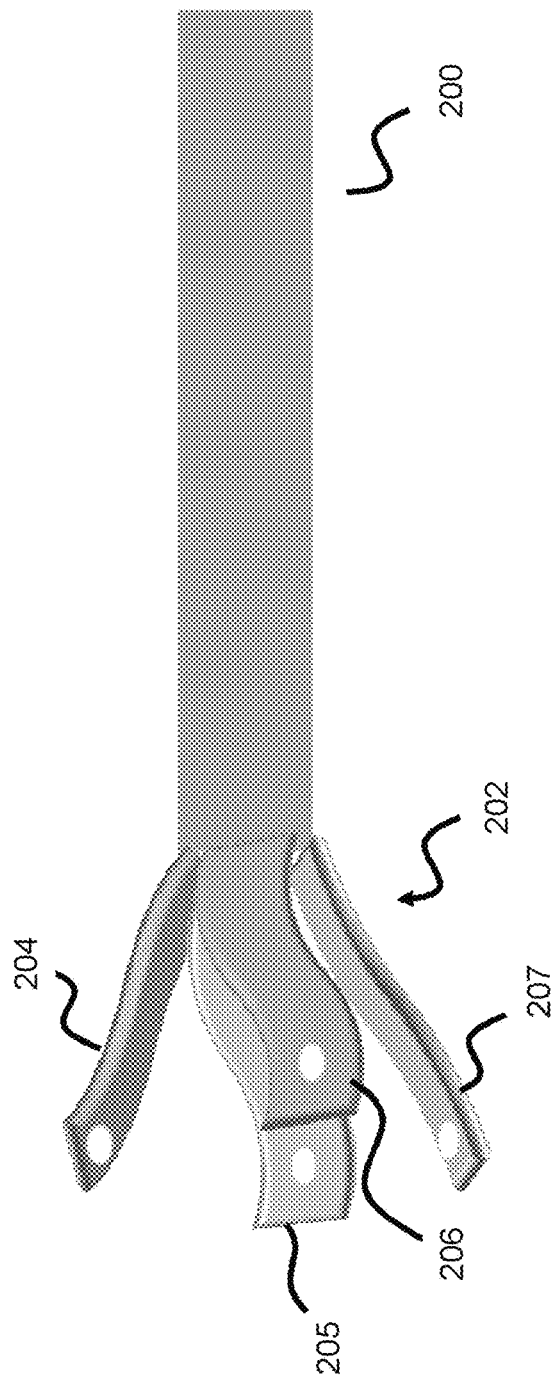
FIG. 10 illustrates a delivery pusher in an expanded state, according to one embodiment.

FIG. 10 offers another view of the final configuration of the delivery pusher, with arms 204-207 extending from the distal end 202 of the pusher 200. Arms 204-207 extend in a radially expanded manner when unconstrained, as shown in FIG. 10, in a manner that will be discussed in more detail later.

Figure 13:
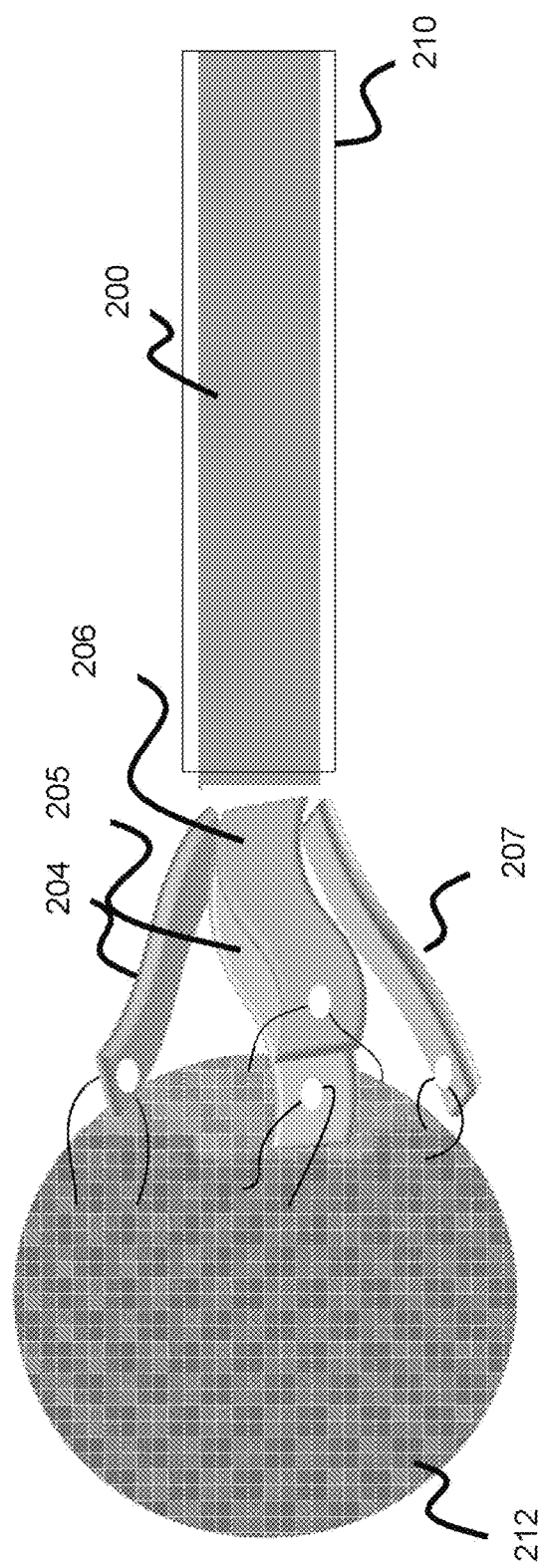
FIG. 13 illustrates a delivery pusher in an expanded state connected to an occlusive device in an expanded state, according to one embodiment.

The distal part of each arm 204-207 has a hole 204 a-207 a, where each hole passes completely through each arm. The function of these holes 204 a-207 a is to each hold a tether which connects to the occlusive device 212 to thereby hold the occlusive device 212, as shown in FIGS. 11-13. For example, such as shown in FIGS. 11-12, a first occlusive device tether 204b may terminate in or pass through hole 204a of arm 204, a second occlusive device tether 205b may terminate in or pass through hole 205b of arm 205, and third and fourth occlusive device tethers may terminate in or pass through respective holes of arm 206 (FIG. 13) and arm 207 (FIG. 13), In FIGS. 11-13, the occlusive device 212 takes the form of an intrasaccular device, intrasaccular devices were discussed in detail earlier. The intrasaccular device can be a mesh comprised of metallic wires—made of, for instance, nitinol, stainless steel, and/or radiopaque material such as tantalum, platinum, gold, or palladium. In another example, drawn-filled tubing, which comprises a radiopaque core material surrounded by a metallic (e.g., nitinol or stainless steel) jacket can be used as part of the metallic mesh.

Arms 204-207 take on a first contracted configuration when housed within a delivery catheter, as shown in FIGS. 11 and 12. In FIG. 11, both the pusher 200 and occlusive device 212 are housed within a delivery catheter 210 and therefore both have a contracted configuration. In FIG. 12, pusher 200 is housed within a delivery catheter and has a contracted configuration, while the occlusive device 212 is freed from the delivery catheter and adopts its naturally heat-set expansile shape. The arms 204-207 take on an expanded configuration when not constrained by the delivery catheter, as shown in FIG. 13. The arms are heat set such that they naturally adopt an expanded shape when unconstrained. The arms can be manufactured in a variety of ways to enable this heat set shape. For instance, the distal part of the pusher can comprise a series of longitudinal cuts spaced around the periphery of the pusher (e.g. 3 cuts spaced 120 degrees apart—as shown in FIG. 8, which would result in four arms)—although fewer or more arms can be used. After the cuts are made, a material which has a larger diameter than the rest of the pusher is wedged into the distal arm region 102 of the pusher to expand the diameter such that the arms protrude outward, and the pusher is heat-treated or heat-set into this shape such that the arms adopt this heat-set shape. The pusher can be made of a variety of materials, however, easily heat-set material such as nitinol is generally preferred at least along the distal region 202 so that the arms 204-207 can easily adopt an expanded shape. In one example, a marker band (e.g. tantalum or platinum) can be placed along a distal portion of the pusher to aid in visualizing the distal part of the pusher so the user can tell when the occlusive device is about to be delivered when utilizing fluoroscopic imaging.

In one embodiment, pusher 200 is a tube with a lumen therein, and the lumen provides a passage for additional materials to be tracked through the pusher. These additional materials can be additional embolic agents, and/or a detachment mechanism to dissociate the occlusive device 212 from the pusher 200 to thereby deploy the occlusive device at the treatment site. The detachment mechanism concept is shown in FIGS. 14-15.

Figure 14:
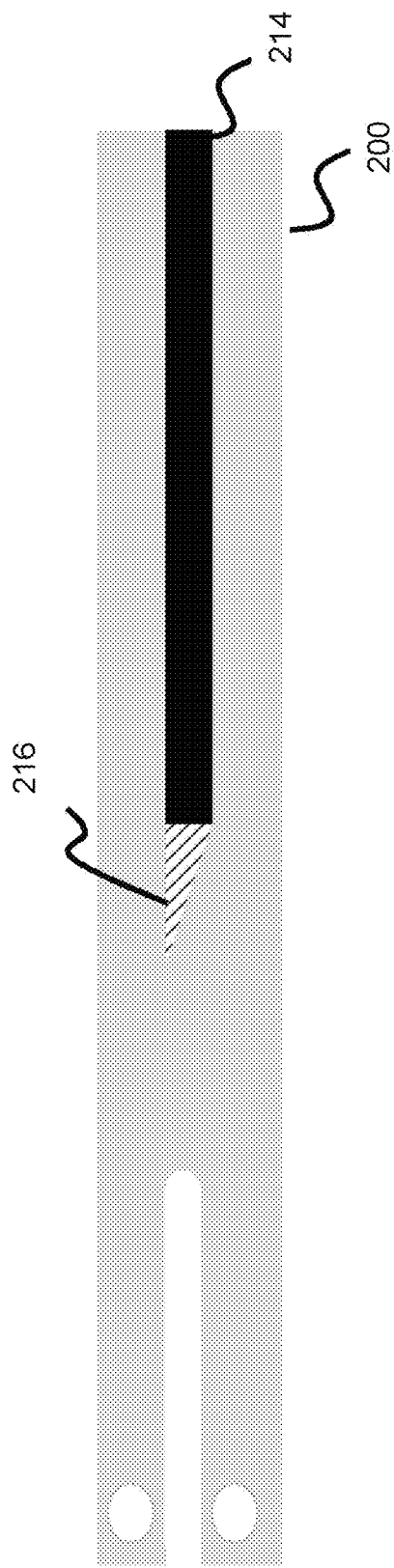
FIG. 14 illustrates a delivery pusher and a mechanical severing mechanism used to detach an occlusive device.

In FIG. 14, pusher 200 includes a lumen which spans the entirety of the pusher and is sized to accommodate a mechanical severing mechanism. The severing mechanism comprises an elongated rod 214 and a blade or knife 216 at the distal end. Blade 216 is used to sever the tethers linking the occlusive device 212 to arms 204-207. This embodiment has particular utility for smaller sized intrasaccular devices (e.g. those used to treat neurovascular aneurysms) where it can be hard to design a non-mechanical (e.g. thermolytic or electrolytic) detachment system due to the limited space available. The elongated rod 214 is mechanically pushed through the pusher 200 so that the blade contacts the tethers to sever the tethers and thereby release the occlusive device. Alternative concepts can utilize a plurality of blades (e.g. 2, 3, or 4 blades). In one example, the number of blades corresponds to the number of tethers.

Figure 15:
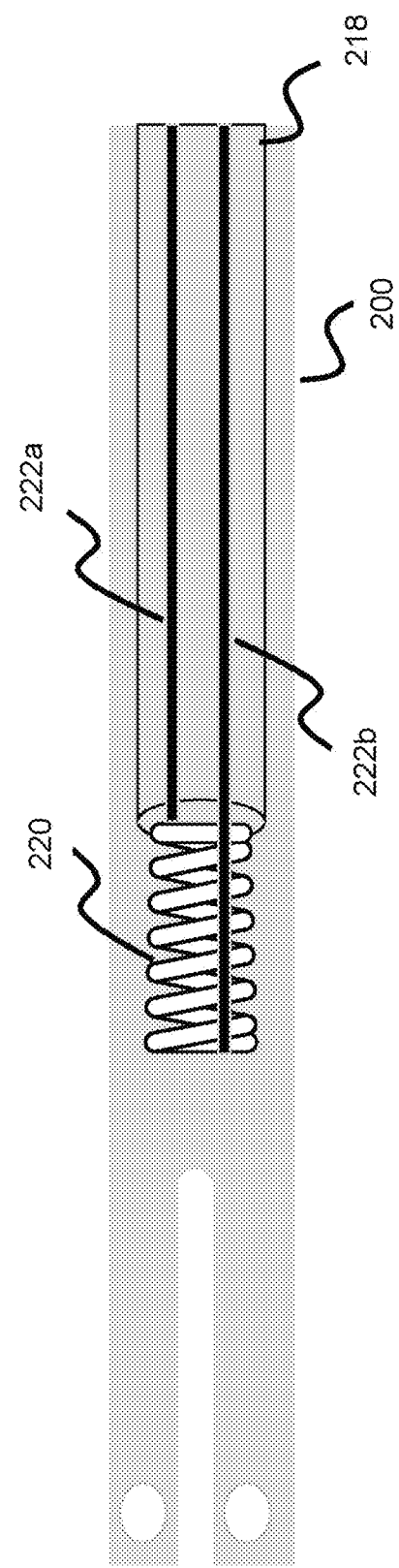
FIG. 15 illustrates a delivery pusher and a heater used to detach an occlusive device.

In FIG. 15, a thermal detachment system is shown. An elongated tube 218 is pushed through pusher 200, the elongated tube 218 has a heater coil 220 at its distal end. The elongated tube has a lumen running between the proximal and distal end which provides passage for a pair of wires 222a, 222b. These wires are proximally connected to a voltage source (e.g., a battery) and distally connected to the heater coil to power the heater coil. The tube 218 is pushed through the delivery pusher 200 so that the heater coil is placed near the tethers connecting the occlusive device to the arms. The heater is then activated to melt or sever the tethers, thereby detaching the occlusive device.

The specification disclosure has dealt with embolic delivery devices/systems/methods and ways to make embolic delivery easier. The specification has also discussed particular utility for these concepts with smaller occlusive devices (e.g. those used in the neurovasculature). Please note, these concepts can be sized either larger or smaller to treat a variety of conditions in a variety of regions of the vasculature, not necessarily limited to the neurovascular space—in other words, these ideas can be used in a variety of regions in the vasculature to facilitate easier embolic usage and delivery.

Although the invention has been described in terms of particular embodiments and applications, one of ordinary skill in the art, in light of this teaching, can generate additional embodiments and modifications without departing from the spirit of or exceeding the scope of the claimed invention. Accordingly, it is to be understood that the drawings and descriptions herein are proffered by way of example to facilitate comprehension of the invention and should not be construed to limit the scope thereof.

What is claimed is:

1. An occlusive delivery device comprising:
   a delivery pusher configured to deliver an occlusive device;
   the occlusive device comprising one or more wires and having a collapsed configuration when within a delivery catheter and an expanded configuration when not within the delivery catheter, wherein the one or more wires includes a plurality of proximal wire ends;
   a connection interface; and
   a retention structure connected to the connection interface and the occlusive device, wherein the retention structure comprises a plurality of bands each freely rotatable about the connection interface, and wherein the plurality of proximal wire ends of the occlusive device are each attached to the retention structure.

2. The occlusive delivery device of claim 1, wherein the occlusive device is an intrasaccular device comprising a mesh of wires.

3. The occlusive delivery device of claim 1, wherein the connection interface is a ring.

4. The occlusive delivery device of claim 1, wherein the connection interface has one or more cut-out regions to allow the connection interface to flex.

5. The occlusive delivery device of claim 1, wherein each band of the plurality of bands includes one or more holes accommodating the one or more wires of the occlusive device.

6. The occlusive delivery device of claim 1, wherein two wire ends of the plurality of proximal wire ends of the occlusive device are attached to each band of the plurality of bands.

7. The occlusive delivery device of claim 1, wherein the connection interface is connected to the delivery pusher with a curved arc wire segment.

8. An occlusive delivery device comprising:
- a delivery pusher configured to deliver an occlusive device;
- the occlusive device comprising one or more wires and having a collapsed configuration when within a delivery catheter and an expanded configuration when not within the delivery catheter, wherein the one or more wires includes a plurality of proximal wire ends;
- a connection interface between the delivery pusher and the occlusive device; and
- a retention structure connected to the connection interface and the occlusive device, wherein the retention structure comprises a plurality of coils each freely rotatable about the connection interface, and wherein the plurality of proximal wire ends of the occlusive device are each attached to the retention structure.

9. The occlusive delivery device of claim 8, wherein the occlusive device is an intrasaccular device comprising a mesh of wires.

10. The occlusive delivery device of claim 8, wherein the connection interface is a ring.

11. The occlusive delivery device of claim 8, wherein the connection interface has one or more cut-out regions to allow the connection interface to flex.

12. The occlusive delivery device of claim 8, wherein two wire ends of the plurality of proximal wire ends of the occlusive device are attached to each coil of the plurality of coils.

13. An occlusive delivery device comprising:
- a delivery pusher configured to deliver an occlusive device;
- the occlusive device comprising one or more wires and having a collapsed configuration when within a delivery catheter and an expanded configuration when not within the delivery catheter, wherein the one or more wires includes a plurality of proximal wire ends;
- a connection interface linked to a distal portion of the delivery pusher; and
- a retention structure connected to the connection interface and the occlusive device, wherein the retention structure comprises a plurality of bands each freely rotatable about the connection interface, and wherein the plurality of proximal wire ends of the occlusive device are each attached to the retention structure.

14. The occlusive delivery device of claim 13, wherein the connection interface is a ring.

15. The occlusive delivery device of claim 14, wherein the ring is attached to the delivery pusher at one or more regions around the ring.

16. The occlusive delivery device of claim 15, wherein the ring is connected to the delivery pusher with a curved arc wire segment.

17. The occlusive delivery device of claim 13, wherein the occlusive device is an intrasaccular device comprising a mesh of wires.

18. The occlusive delivery device of claim 13, wherein the occlusive device is an intrasaccular device for occluding an aneurysm.

19. The occlusive delivery device of claim 13, wherein the occlusive device is an intrasaccular device for occluding a cerebral aneurysm.

20. The occlusive delivery device of claim 13, wherein each band of the plurality of bands is attached to at least two wire ends of the plurality of proximal wire ends of the occlusive device.

* * * * *